United States Patent [19]

Miller

[11] Patent Number: 4,991,573
[45] Date of Patent: Feb. 12, 1991

[54] ORTHOPEDIC SUPPORT BELT

[76] Inventor: Donald L. Miller, Redmond, Wash.

[21] Appl. No.: 498,695

[22] Filed: Mar. 26, 1990

[51] Int. Cl.$^5$ .......................... A61F 5/02; A61F 5/28; A61F 5/30
[52] U.S. Cl. .................... 128/78; 128/99.1; 128/106.1; 128/112.1
[58] Field of Search ...................... 128/78, 24 R, 99.1, 128/100.1, 101.1, 102.1, 106.1, 111.1, 112.1, 115.1, 116.1, 117.1; 272/143; 2/44

[56] References Cited

U.S. PATENT DOCUMENTS

| | | | |
|---|---|---|---|
| 95,432 | 10/1869 | Cooper | 128/112.1 X |
| 108,253 | 10/1870 | Goodier | 128/106.1 |
| 729,017 | 5/1903 | Turner | 128/106.1 |
| 1,106,314 | 8/1914 | O'Brien | 128/101.1 |
| 2,733,712 | 2/1956 | Wuesthoff | 128/78 |
| 3,154,072 | 10/1964 | Mack | 128/117.1 X |
| 3,578,773 | 5/1971 | Schultz | 128/78 |
| 3,605,731 | 9/1971 | Tigges | 128/24 R |
| 3,765,721 | 10/1973 | Watkin | . |
| 4,159,020 | 6/1979 | von Soiron et al. | 128/99.1 X |
| 4,178,922 | 12/1979 | Curlee | . |
| 4,475,543 | 10/1984 | Brooks et al. | 128/78 |
| 4,552,135 | 11/1985 | Racz et al. | 128/78 |
| 4,572,167 | 2/1986 | Brunswick | 128/78 |
| 4,622,957 | 11/1986 | Curlee | . |
| 4,682,587 | 7/1987 | Curlee | . |
| 4,682,588 | 7/1987 | Curlee | . |
| 4,685,668 | 8/1987 | Newlin, Jr. | . |
| 4,768,499 | 9/1988 | Kemp | 128/100.1 X |
| 4,794,916 | 1/1989 | Porterfield et al. | 128/101.1 X |
| 4,941,465 | 7/1990 | Borschneck | 128/99.1 X |

FOREIGN PATENT DOCUMENTS 41210  10/1912  United Kingdom ............... 128/99.1

Primary Examiner—Richard J. Apley
Assistant Examiner—Linda C. Maas Dvorak

[57] ABSTRACT

An improved support belt adapted for attachment to the lumbar region of the human body. The support belt is formed with two layers of elongated rectangular panels housing therebetween a semi-rigid cushioned extension pad. The belt is structured with an outer layer of permeable webbed porous material with an inner layer of soft absorbent material. The extension pad is structured with an inner panel of rigid plastic with an outer covering of soft resilient foam padding. The extension pad also contains a V-shaped groove positioned parallel with the spine in use.

2 Claims, 4 Drawing Sheets

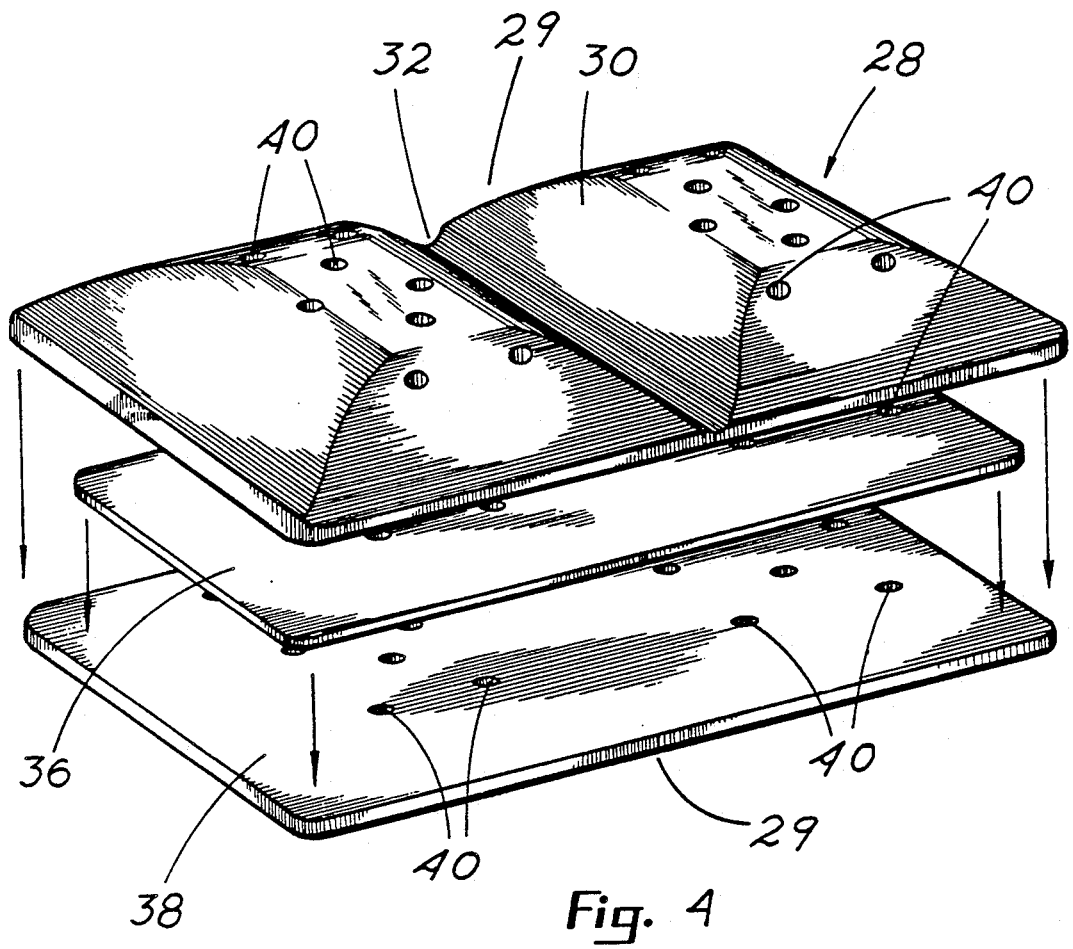
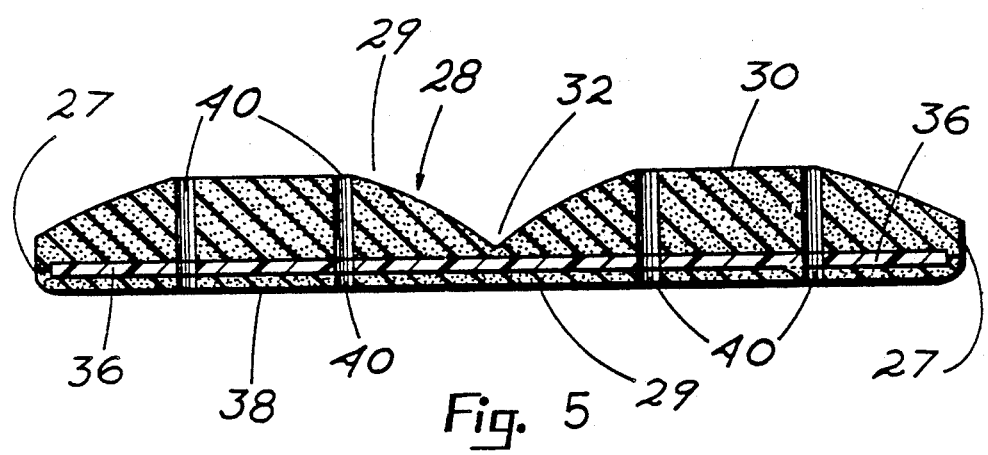

ORTHOPEDIC SUPPORT BELT

BACKGROUND OF THE INVENTION

1. Field of the Invention:

This invention relates to support belts worn by humans about the waist area to help prevent compression and abnormal curvature of the spine in the lumbar area. The present invention is also useful for supporting the main muscle groups of the torso.

2. Description of the Prior Art:

The human spinal column is part of the skeletal system which supports and protects the body and is comprised of thirty-three bones consisting of seven cervical, twelve thoracic, and five lumbar vertebrae, with the later merging endwardly into the five fused sacral and the four fused coccyx vertebrae. The twenty-four individual vertebrae have various bony projections, one projecting directly outward from the back of the spine known as the spinous process. This spinous process of each vertebrae can be felt along the back as hard knobs. The individual vertebrae are connected and supported by various cartilages, muscles and ligaments which allow flexibility for bending and twisting of the torso. Between each vertebra is an intervertebral disc which functions to cushion and separate each vertebra, helping to prevent compression of the peripheral spinal nerves branching off from the spinal cord housed within the spinal column. Displacement of one or more of the individual vertebrae from its normal position can create pressure against the spinal nerves, most often resulting in pain. Displacement is often caused from unequal tension of the muscles supporting the spinal column causing one or more of the individual vertebrae to be pulled out of alignment with the rest. This unequal tension of the muscles can be caused from a variety of factors including over-exertion, uneven muscular stress, emotional tension and physical injuries. A great majority of back pain experienced by the general public occurs in the lower portion of the back generally referred to as the lumbar area or the spinal segments L-3 through S-1 specifically. Once the vertebrae are re-aligned the pressure exerted against the nerves is generally alleviated, resulting in reduction or elimination of pain. Statistics show that most common non-injury back aches and pains are accompanied by the absence of a desirable spinal curve and a lack of muscular support. Normal treatment of some injury and most non-injury back conditions includes applying pressure to the affected area. Support belts of various types have long been used to apply pressure against the spine and muscles of the lower back area, but fail to promote the correct curvature and extension of the spine. Some of these support belts are also used to prevent injury and stress from occurring in the first place. Many of the support belts used as preventative measures are directed towards use during strenuous exercise or activities, especially weight lifting.

Many of the support belts used in the past were merely widened belts which were tightened to provide counter pressure, and did not promote correct extension of the spine. This type of device is exemplified by the U.S. Pat. No. 4,685,668, issued on a weight lifting belt to T. L Newlin, Jr. on Aug. 11, 1987. These belts were relatively rigid and too much pressure was applied directly on the spinous processes of the vertebrae, which was especially evident when the wearer bent over, resulting in pain along the spine. Wearing this type of belt for an extended period of time also tended to constrict blood flow and cause skin irritation.

Later improvements provided belts adapted with structures which were inflatable with fluid or air for adjusting the amount and degree of pressure exerted against a specific area of the spine. The material used in inflatable structures is necessarily non-porous and tends to create moisture condensation which eventually increases perspiration, becoming uncomfortable to the wearer. Inflatable structures are more time consuming to apply than non-mechanical belts and often require a second party to operate. Inflatable structures also run the risk of experiencing occasional leaks which would render the unit no more effective than a large belt. Prior art devices having inflatable structures are characteristic of four inflatable therapeutic belts patented by J. D. Curlee. The Curlee devices are included in U.S. Pat. No. 4,178,922 dated Dec. 18, 1979, U.S. Pat. No. 4,622,957, dated Nov. 18, 1986, and two U.S. Pat. Nos. 4,682,587 and 4,682,588 dated Jul. 28, 1987. The Curlee devices do not specifically attempt to differentiate between the pressure applied by the inflatable structures against the spine or the pressure applied to the muscle area on either side of the spine. In other words, Curlee does not specifically attempt to protect the spine from the compression forces exerted on the rest of the back, which can be greatly increased when the wearer is bending over. This excessive pressure directly on the spine can be quite uncomfortable to the wearer. If it were to be argued inflatable structures are to be considered moderately flexible and compressible inherently by nature so as to avoid excess compression of the spine originally, then such inflatable structures would also be lacking adequate lateral support for the rest of the back. The essential non-porous nature of the inflatable structures prevents evaporation of perspiration of the wearer and retains heat, becoming uncomfortable to the wearer quite quickly. Some inflatable structures of support belts, especially those having larger stretchable chambers, also tend to have a constricting effect on the body similar to that of a blood pressure cuff. Prolonged use of such units can result in complications such as muscle spasms, and blockage of blood circulation among others.

B. C. Watkin developed a lumbar support pad on which he was issued U.S. Pat. No. 3,765,721, dated Oct. 16, 1973. Watkin addressed the problem of avoiding direct compression of the spine and subsequently developed a pad having a central vertical channel for protection of the spine during compression of the pad against the back. Watkin's device however, is formed of a solid section of foamed plastic material which in itself could prove too rigid if the foamed plastic were too dense, and too flexible if the foam were too soft and porous. The former would be stiff and uncomfortable to the wearer and the later would be ineffective as a back support means. Watkin's pad would also tend to create chaffing of the skin due to prevention of moisture evaporation. Watkin also fails to suggest or anticipate attachment of his pad to a belt so as to be worn on the user, but instead refers twice to attachment of the pad to a stationary object such as the backrest of a seat.

One basic problem found with support belts of all types is providing a device rigid enough to include sufficient support for correct alignment of the spine while at the same time maintaining comfort. Elimination or reduction of direct compression of the spine and irritation of the skin due to the non-porous nature of the materials of manufacture has also been a problem with many past art support belts. Therefore it is desireable to provide a support belt which is comfortable yet rigid enough to maintain the spine in correct alignment and extension. While an effective equilibrium has yet to found in the past art devices, I feel my device overcomes these disadvantages and provides other new and useful features not included in the past art devices.

SUMMARY OF THE INVENTION

I have provided a support belt for the lower back or lumbar region of the spine which helps to maintain correct alignment and extension of the lower spine between thirty-five and forty-five degrees. Too little or too excessive of a curvature of the spine creates stress not only on the spine and associated nerves but to the surrounding supporting musculature as well. This optimum curvature, also often referred in the medical field as the lordotic curve, is considered to be the optimum angle for normal functioning of the lower spine and supporting muscles for the average adult person. My support belt helps to maintain the spine in normal extension with the addition of an orthopedic lumbar extension pad. By putting the spine in normal extension with this pad, the spinal erector musculature, such as the abdominals, intercostals and gluteals, are more efficiently involved to support the vertebral structure. With this structural support gravitational stresses become distributed to the muscles rather than localized in pain sensitive areas of the spine. This not only helps to prevent injury and excess stress to the lower back during strenuous exercise but also helps to reduce pain and promote healing after certain injuries have occurred by providing support to the spine giving the muscles a chance to rest. The extension pad belt is also particularly useful for those who experience pain from sitting for an extended period of time, where the supporting musculature fatigues and fails to maintain correct alignment. The extension pad is also structured to avoid direct compression of the spine and the outwardly projecting spinous processes, by incorporating a vertical channel into the pad which is positioned directly over the spine when worn. This feature is especially effective when the wearer bends over, providing extra room for the extending spine. The extension pad is also structured for sufficient rigidity while maintaining comfort by laminating several layers of plastics having variable densities. Two outer layers of closed-cell polyurethane foam enclose a thin inner layer of rigid plastic. The foam is firm yet sufficiently soft so as to be comfortable to the wearer and is contoured to sustain the lordotic curve, maintaining this contour even after repeated compressions. The rigid inner plastic panel is only slightly flexible longitudinally for waist adjustment, and provides sufficient vertical support to maintain the spine in the correct anatomical extension. The support belt is also specifically structured to avoid moisture condensation and skin irritation by perforation of the extension pad and lamination of the belt with an outer layer of porous material with an inner layer of moisture absorbing fabric. The support belt is not only structured for comfort and effective spinal support, but is also provided in a wide range of colors for aesthetic reasons.

Two slightly different embodiments of the invention are provided. One is primarily directed for use during strenuous activities and contains an especially strong attachment structure for connecting the belt ends together. This first embodiment is also more aesthetic in appearance being structured to be worn on the exterior of the clothing. The second embodiment is for more sedentary use such as driving, and is primarily intended to be worn under the user's clothes. Both support belts are easy to apply and are machine washable.

Therefore, it is a primary object of the invention to provide a support belt which maintains the lower spine in correct anatomical lumbar extension, thereby reducing or eliminating pain.

Another object of the invention is to provide the above with a support belt which avoids exerting excessive pressure on the lower spine.

A further object of the invention is to provide the above with a support belt which is comfortable for the wearer by providing materials which allow sufficient air circulation and moisture evaporation to reduce or prevent chaffing of the skin.

An even further object of the invention is to provide the above with a support belt which is machine washable and provided in a variety of colors.

A still further object of the invention is to provide the above with a support belt which can be worn for extremely strenuous activities thereby helping to prevent injury, or for long term sedentary applications to prevent fatigue of certain muscles.

Other objects and advantages of this invention will become apparent by reading descriptions of the numbered parts in the remaining specification along with comparison of like numbered parts shown in the accompanying drawings.

BRIEF DESCRIPTION OF THE DRAWINGS

FIG. 4 is an exploded perspective view of the component parts of the extension pad.

FIG. 5 is a cross-sectional side view of the assembled extension pad, with the cross-section taken midsection longitudinally.

DESCRIPTION OF THE PREFERRED EMBODIMENTS

Figure 1:
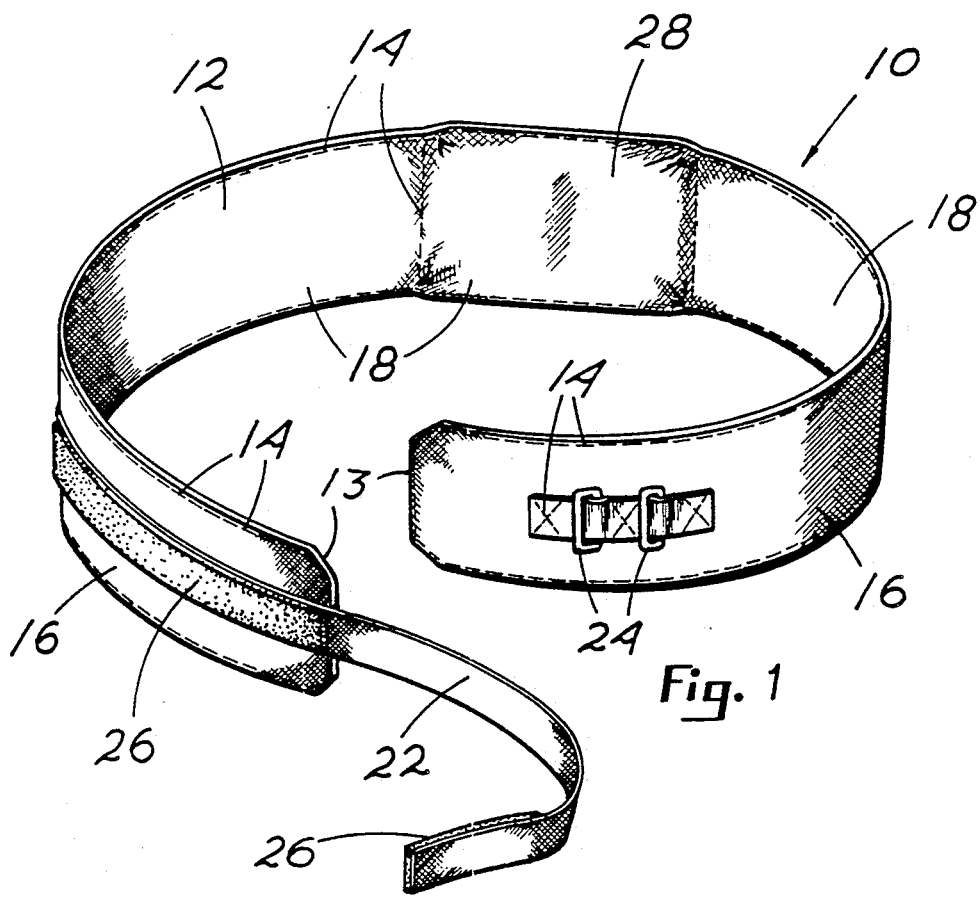
FIG. 1 is a frontal perspective view of the first embodiment of the invention which is structured with dual belt end attachments of a strap with clasp and hook and loop style fasteners affixed to the end of the strap as shown. This embodiment is structured for use during strenuous physical exertion.

Referring now to the drawings and to FIG. 1 where the first embodiment 10 of the invention provides an improved orthopedic support structure as shown. First embodiment 10 consists of an elongated rectangular belt 12 which is comprised of two layers or panels of material forming an enclosed interior envelope affixed edgewardly by conventional stitching 14. Although the method of attachment of the layers of belt 12 is shown in the drawings as stitching 14, other suitable methods such as adhesives or heat bonding can also be used. The outer surface layer of belt 12, exterior belt covering 16, is preferably comprised of a flexible, but non-stretchable heavy duty webbed porous material such as canvas, nylon, or Cordura, manufactured by Dupont Inc. The inner surface layer of belt 12, referred to as interior belt covering 18, is positioned adjacent the skin or clothing of user 20 when in use. Interior belt covering 18 is preferably comprised of a soft, porous, flexible material such as a cotton blend which absorbs perspiration and dissipates heat, thereby reducing or eliminating skin chaffing and irritation. Interior belt covering 18 functions similar to a wick, drawing heat and moisture away from the skin while the porous exterior belt covering 16 promotes evaporation of the moisture. An average belt 12 is sized approximately thirty-six inches in length and four to five inches in width with slight variances to accommodate different sizes of users 20. The free ends 13 of first embodiment 10 are affixed with a dual attachment structure for releasable attachment to the lower torso of user 20, as seen in FIG. 1. The dual attachment structure consists of a narrow elongated strap 22 affixed to one free end 13 of belt 12. Approximately one half the length of strap 22 is affixed to exterior belt covering 16 with the remaining length of strap 22 extending outward unattached. The exterior distal end of strap 22 is affixed with a short section of releasable hook and loop fasteners 26 with the corresponding mating section of fasteners 26 affixed on the opposite attached end of strap 22. On the opposite free end 13 of belt 12, affixed to exterior belt covering 16, are two loop clasps 24. The distal end of strap 22 is threaded through one of the two clasps 24, then drawn back over itself, attaching the free distal end to the side of belt 12 with hook and loop fasteners 26. Two loop clasps 22 are provided for greater adjustability of the belt 12. The section of hook and loop fastener 26 affixed to the attached end of strap 22 is longer in length than its corresponding mating section located on the distal end of strap 22, allowing for girth adjustment of belt 12 around user 20. While the use of strap 22 with clasps 24 alone would be sufficient for maintaining belt 12 in position on user 20, the addition of hook and loop fasteners 26 provides added security and stability during strenuous activities and also prevents the distal free end of strap 22 from hanging loose.

Extension pad 28 is a substantially rectangular contoured padded plate having two oppositely disposed wide surfaces 29 with relatively narrow side edges 27. Extension pad 28 is comprised of two outer layers of flexible closed-cell polyurethane foam which provides a layer of padding over an inner layer of rigid plastic. The padded front surface of extension pad 28 is referred to as contoured panel 30 with the oppositely disposed outer padded layer being known as backing panel 38. Contoured panel 30 is thicker than backing panel 38 and makes up approximately two-thirds the thickness of the assembled extension pad 28. Contoured panel 30 contains a central vertical groove known as V-groove 32, best shown in FIG. 4 and 5. The divided surface edges of contoured panel 30 are beveled to provide a specific contoured shape, best shown in FIG. 4. The interior layer of extension pad 28 consists of one rigid plastic reinforcement panel 36, also shown in FIG. 4. Reinforcement panel 36 is a flat plastic plate having suitable density to be moderately rigid, and is only slightly flexible longitudinally. The back surface of extension pad 28 or backing panel 38, is comprised of the same closed-cell polyurethane foam as contoured panel 30 and primarily functions to cushion the exterior surface of reinforcement panel 36. All three layers of extension pad 28, shown in FIG. 4, are laminated into a single unit, either with adhesives, heat sealing or other suitable methods. All three layers of extension pad 28 contain aligned apertures or perforations 40, as shown in FIG. 4 and 5, which serve to promote air circulation and heat evaporation. Extension pad 28 is positioned longitudinally on belt 12 between exterior belt covering 16 and interior belt covering 18, with contoured panel 30 adjacent interior belt covering 18 and backing panel 38 adjacent exterior belt covering 16, as shown in an exploded view in FIG. 3. Extension pad 28 is shown in drawing FIGS. 1 and 2 stabilized in position with stitching 14, although other suitable attachment means, such as adhesives, can also be used. Extension pad 28 is sized approximately seven inches in length, one inch in width and about four and a half inches in height and is positioned longitudinally on belt 12 with V-groove 32 of contoured panel 30 positioned generally perpendicular to the lengthwise edge of extension pad 28.

Figure 6:
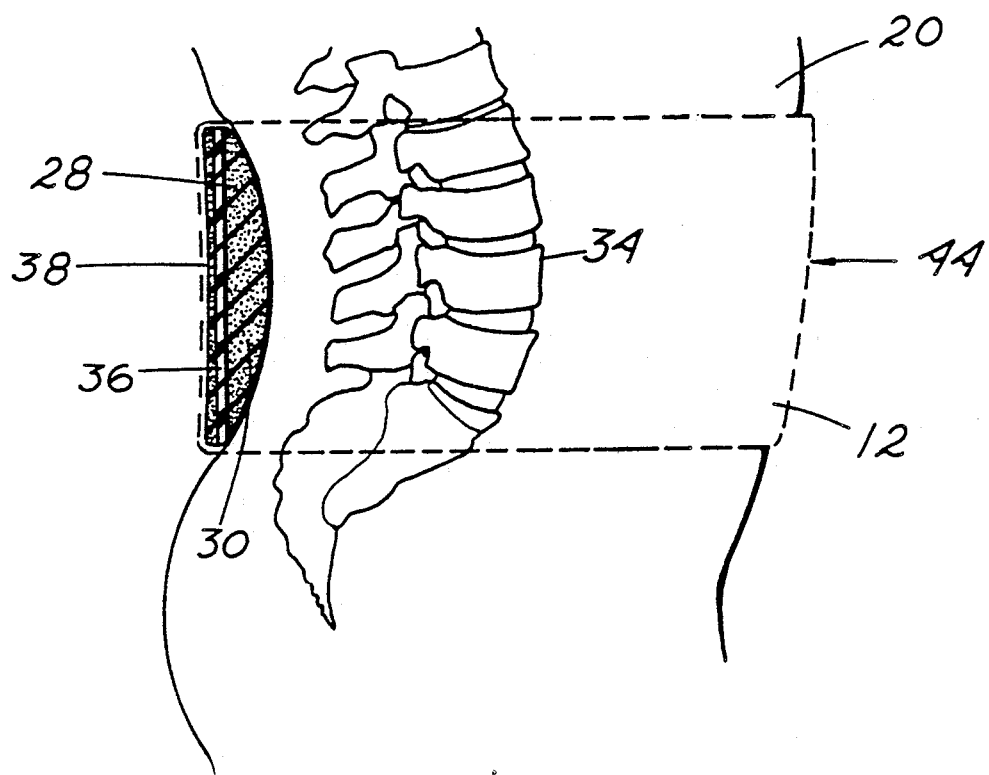
FIG. 6 illustrates the support belt in a side view, shown in phantom lines, being worn on the user with the extension pad shown in cross section.
Figure 7:
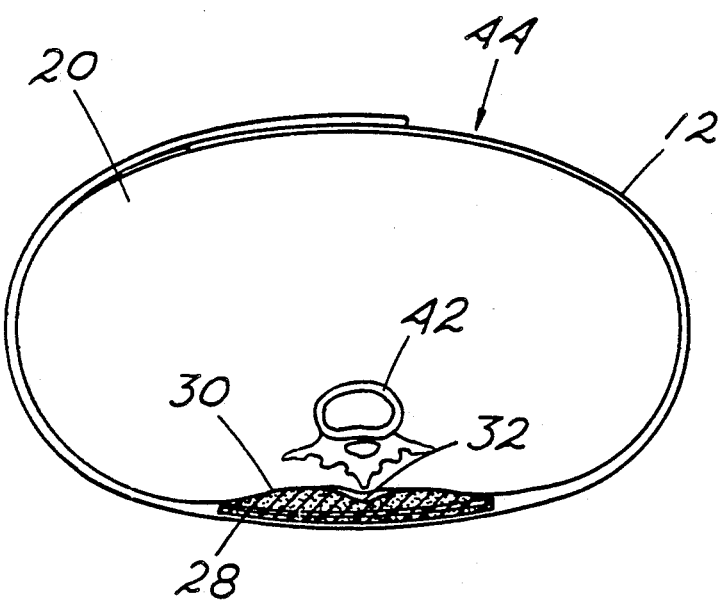
FIG. 7 illustrates the support belt in a top plan view being worn by the user, illustrating the position of the spinal V-groove shown adjacent a vertebra.

Extension pad 28, when affixed to belt 12, is adapted to promote the correct lordotic curve of spine 34, as seen in FIG. 6. The size, structure and composition of extension pad 28 is crucial to the effectiveness of belt 12 in promoting optimum spinal extension and relief of pain. Reinforcement panel 36 provides the rigidity required for sufficient support and extension of spine 34 while the soft padding of contoured panel 30 provides not only cushioning against the rigid reinforcement panel 36 but the special beveled contouring is specifically adapted for positioning against the lumbar area of spine 34 for also promoting the correct extension of spine 34, best shown in FIG. 6. Once belt 12 is applied to the waist of user 20 and tightened, counter pressure is applied against the lower back and the abdominal muscles, releasing the tension and strain on specific areas of spinal support musculature. This not only promotes correct posture but also often alleviates pain associated with pulled muscles and misalignment of spine 34. V-groove 32 of contoured panel 30 is positioned adjacent and parallel to spine 34 in use and serves as a relief area to protect spine 34 from excessive compression when belt 12 is tightened or when user 20 bends over. This is best illustrated in FIG. 7 where V-groove 32 is shown adjacent vertebra 42. The relatively small size of extension pad 28 allows for free movement of user 20 but is also rigid enough to provide sufficient support for the lumbar region.

Figure 2:
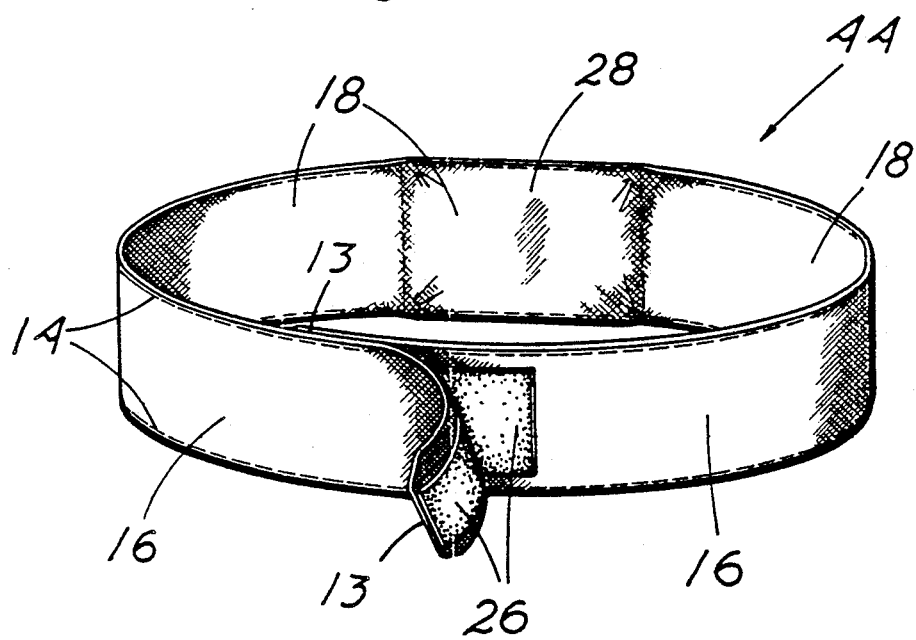
FIG. 2 is a frontal perspective view of the second embodiment of the invention illustrating the second embodiment with hook and loop type fasteners as the attachment structure. This embodiment is structured for mild or moderate exertion and can be worn under clothing.
Figure 3:
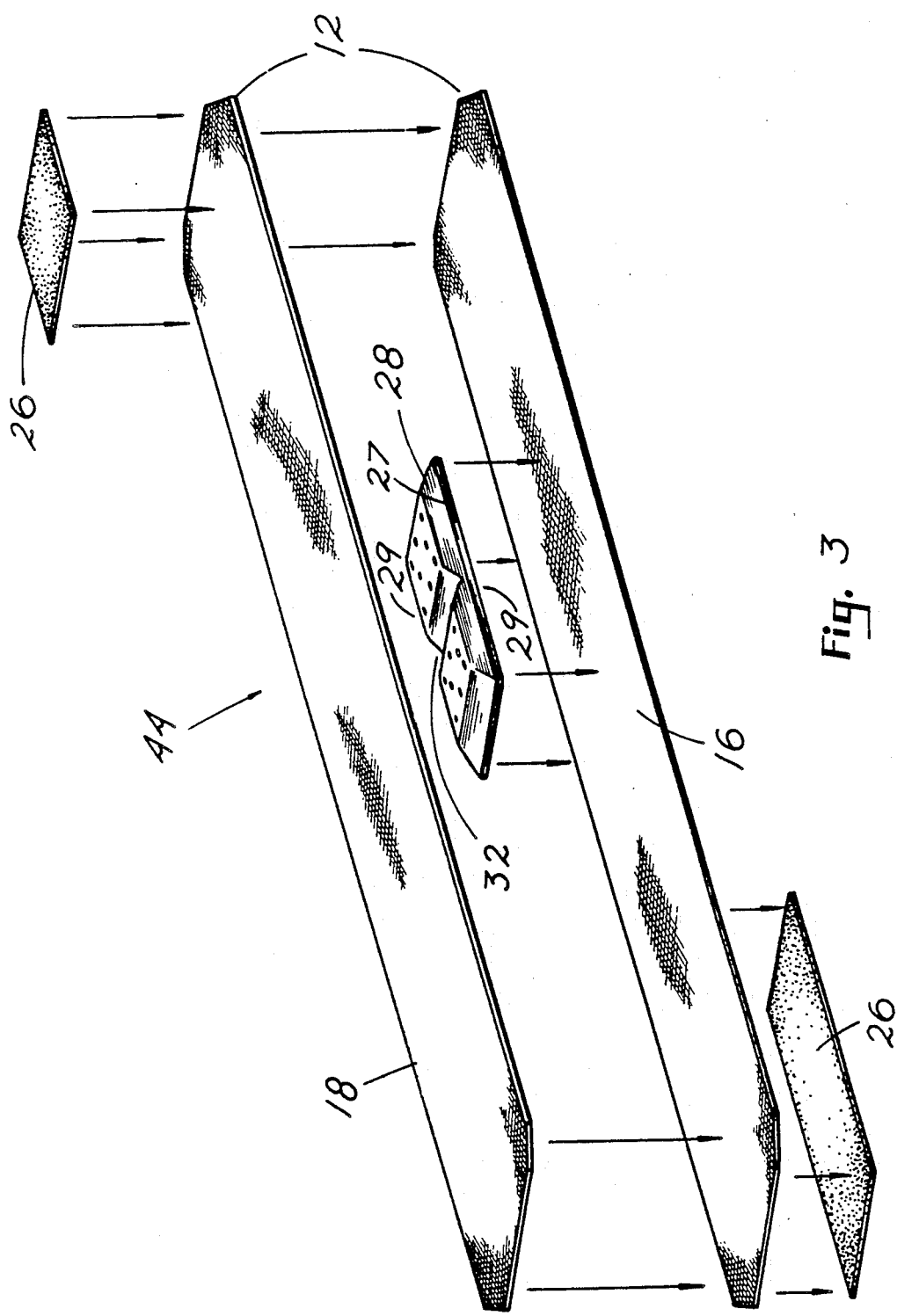
FIG. 3 is an exploded perspective view of the component parts of the second embodiment.

Second embodiment 44, shown in FIG. 2, is structured similar to first embodiment 10 having exterior belt covering 16, interior belt covering 18 and extension pad 28. The means of attachment for embodiment 44 onto user 20 is provided by wide sections of hook and loop fasteners 26 as shown in FIG. 2. Second embodiment 44 is structured primarily for use under clothing and for less active or sedentary activities such as driving. Since second embodiment 44 is designed to be worn under clothing, removal of strap 22 and clasps 24 is necessary to reduce bulk. Since a more sedate activity is suggested when wearing second embodiment 44, there is less danger of hook and loop fasteners 26 coming detached and causing injury such as could be the case with first embodiment 10 if user 20 were, for instance, weight lifting and belt 12 became detached. The sudden release of support could cause excessive strain on the muscles and cause injury, therefore first embodiment 10 has been re-enforced with a double attachment structure.

Obviously, additional modifications and variations of the present invention are possible in light of the above teachings. It is therefore to be understood that within the scope of the appended claims, the present invention may be practiced otherwise than as specifically described and shown.

What is claimed is:

1. An orthopedic support structure for human use, comprising in combination:

an elongated first panel, said first panel being of a flexible generally non-stretchable material, said first panel further being generally porous to provide for a degree of air and moisture movement therethrough;

a pad comprising a generally rigid reinforcing panel generally covered on at least one surface thereof with a resilient padding layer, said pad having narrow side edges and two oppositely disposed wide surfaces, said padding layer having a generally centered groove extending across a surface thereof with the grooved surface being oppositely disposed from said reinforcing panel, the grooved surface of said padding layer being one of said two oppositely disposed wide surfaces of said pad; said pad having a plurality of apertures therethrough, said apertures through said pad extending from one said wide surface through the other said oppositely disposed wide surface of said pad, said apertures adapted to provide for a degree of air movement through said pad;

an elongated second panel, said second panel being of a flexible material sufficiently soft to be generally nonabrasive to human skin, said second panel further being generally porous to provide for a degree of air and moisture movement therethrough, said second panel further being of a said material adapted to absorb moisture from a surface;

said pad placed between said first panel and said second panel with said first panel and said second panel being aligned lengthwise, said pad being placed between two oppositely disposed free ends of said aligned first and second panel, said aligned first panel and said second panel affixed together with said pad therebetween, said pad being affixed between said affixed together first panel and second panel with the grooved surface of said padding layer being adjacent said second panel; said affixment of said first panel to said second panel with said pad therebetween providing a belt having said two oppositely disposed free ends;

attachment means affixed to at least one of said two oppositely free ends of said belt with said attachment means adapted to provide releasable attachment of said two oppositely disposed free ends together;

said belt adapted for affixing about a human torso with said second panel adjacent said human torso and the grooved surface of said padding layer placed adjacent a lumbar area of said human torso, said groove of the grooved surface adapted to provide an area for spine placement when said belt is affixed about said human torso.

2. An orthopedic support structure for human use, comprising in combination:

an elongated substantially rectangular belt member having an exterior surface and an interior surface and two oppositely disposed free ends; said exterior and interior surfaces of said belt member adapted for dissipation of heat and evaporation of perspiration therethrough;

attachment means affixed to at least one of said two oppositely disposed free ends of said belt member with said attachment means adapted to provide releasable attachment of said two oppositely disposed free ends together;

a pad having narrow side edges and two oppositely disposed wide surfaces; said pad comprising a generally rigid reinforcing plate generally covered on at least one surface thereof with a padding layer, said padding layer having a groove extending across a surface thereof with the grooved surface being oppositely disposed from said reinforcing panel, said pad having a plurality of apertures therethrough, said apertures through said pad extending from one said wide surface through the other said oppositely disposed wide surface of said pad, said apertures adapted to provide for a degree of air movement through said pad;

said pad affixed to said belt member between said two oppositely disposed free ends;

said belt member adapted for affixing about a human torso with the grooved surface of said padding layer placed adjacent a lumbar area of said human torso, said groove of the grooved surface adapted to provide an area for spine placement when said belt member is affixed about said human torso.

* * * * *